United States Patent
Ajima (10) Patent No.: US 10,993,632 B2
(45) Date of Patent: May 4, 2021

(54) ELECTRONIC DEVICE FOR DETECTING A PULSE WAVE OF A SUBJECT

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 283 days.

(21) Appl. No.: 15/576,905

(22) PCT Filed: May 11, 2016

(86) PCT No.: PCT/JP2016/002307
§ 371 (c)(1),
(2) Date: Nov. 27, 2017

(87) PCT Pub. No.: WO2016/194308
PCT Pub. Date: Dec. 8, 2016

(65) Prior Publication Data
US 2018/0146871 A1    May 31, 2018

(30) Foreign Application Priority Data
May 29, 2015  (JP) .............................. JP2015-109500

(51) Int. Cl.
*A61B 5/00*  (2006.01)
*A61B 5/024*  (2006.01)
(Continued)

(52) U.S. Cl.
CPC ........ *A61B 5/02444* (2013.01); *A61B 5/0004* (2013.01); *A61B 5/02007* (2013.01);
(Continued)

(58) Field of Classification Search
None
See application file for complete search history.

(56) References Cited

U.S. PATENT DOCUMENTS 4,561,447 A * 12/1985 Kawamura ............ A61B 5/021
600/500
5,309,916 A * 5/1994 Hatschek ............... A61B 5/021
600/485
(Continued)

FOREIGN PATENT DOCUMENTS

| CN | 107530007 A | 1/2018 |
| JP | 2000-005139 A | 1/2000 |

(Continued)

OTHER PUBLICATIONS

Freckmann, G., (2007). Continuous Glucose Profiles in Healthy Subjects under Everyday Life Conditions and after Different Meals. Journal of Diabetes Science and Technology, 1(5), 695-703. doi: 10.1177/193229680700100513 (Year: 2007).*

(Continued)

*Primary Examiner* — Etsub D Berhanu
*Assistant Examiner* — James Stewart Stambaugh, III
(74) *Attorney, Agent, or Firm* — Studebaker & Brackett PC (57) ABSTRACT

An electronic device includes a wearing portion to be worn by a subject and a sensor unit that includes a sensor configured to detect a pulse wave of the subject. The sensor unit includes a displacement portion configured to contact a measured part of the subject and to be displaced in accordance with the pulse wave of the subject when the wearing portion is worn by the subject.

13 Claims, 9 Drawing Sheets (51) Int. Cl.
- *A61B 5/145* (2006.01)
- *A61B 5/0285* (2006.01)
- *G16H 50/20* (2018.01)
- *A61B 5/02* (2006.01)
- *A61B 5/0295* (2006.01)
- *A61B 5/11* (2006.01)

(52) U.S. Cl.
CPC ........ *A61B 5/02035* (2013.01); *A61B 5/0285* (2013.01); *A61B 5/0295* (2013.01); *A61B 5/1121* (2013.01); *A61B 5/14532* (2013.01); *A61B 5/14546* (2013.01); *A61B 5/4866* (2013.01); *A61B 5/681* (2013.01); *A61B 5/6824* (2013.01); *A61B 5/6831* (2013.01); *A61B 5/6843* (2013.01); *A61B 5/7278* (2013.01); *G16H 50/20* (2018.01); *A61B 5/0022* (2013.01); *A61B 5/02438* (2013.01); *A61B 2560/0252* (2013.01); *A61B 2560/0462* (2013.01)

(56) References Cited

U.S. PATENT DOCUMENTS

| | | | | |
|---|---|---|---|---|
| 5,406,952 | A * | 4/1995 | Barnes | A61B 5/021 600/485 |
| 5,497,779 | A * | 3/1996 | Takaya | A61B 5/021 600/485 |
| 5,776,070 | A * | 7/1998 | Kitazawa | A61B 5/02422 600/483 |
| 6,491,647 | B1 * | 12/2002 | Bridger | A61B 5/021 128/900 |
| 2001/0016689 | A1 * | 8/2001 | Heikkila | A61B 5/14532 600/483 |
| 2002/0177764 | A1 * | 11/2002 | Sohrab | A61B 5/14532 600/345 |
| 2002/0188210 | A1 | 12/2002 | Aizawa | |
| 2004/0006262 | A1 * | 1/2004 | Guy | A61B 5/14532 600/345 |
| 2004/0171946 | A1 * | 9/2004 | Narimatsu | A61B 5/02 600/500 |
| 2006/0094938 | A1 | 5/2006 | Shimada et al. | |
| 2006/0258945 | A1 * | 11/2006 | Nishii | A61B 5/02438 600/500 |
| 2007/0032749 | A1 * | 2/2007 | Overall | A61B 5/02444 600/595 |
| 2011/0251522 | A1 * | 10/2011 | Fujita | A47C 9/002 600/587 |
| 2012/0059237 | A1 | 3/2012 | Amir et al. | |
| 2016/0051171 | A1 * | 2/2016 | Pikov | A61B 5/14532 600/365 |
| 2016/0058385 | A1 | 3/2016 | Ajima | |
| 2018/0116571 | A1 | 5/2018 | Ajima | |

FOREIGN PATENT DOCUMENTS

| | | |
|---|---|---|
| JP | 2002-360530 A | 12/2002 |
| JP | 2004-305268 A | 11/2004 |
| JP | 3692125 B2 | 9/2005 |
| JP | 2006-129887 A | 5/2006 |
| JP | 2008-183256 A | 8/2008 |
| JP | 2012-075820 A | 4/2012 |
| JP | 2012105762 A | 6/2012 |
| WO | 2014/171465 A1 | 10/2014 |

OTHER PUBLICATIONS

Langsted, A., Freiberg, J. J., & Nordestgaard, B. G. (2008). Fasting and Nonfasting Lipid Levels. Circulation, 118(20), 2047-2056. doi: 10.1161/circulationaha.108.804146 (Year: 2008).*
International Search Report issued in PCT/JP2016/002307; dated Jul. 26, 2016.
Written Opinion issued in PCT/JP2016/002307; dated Jul. 26, 2016; with English language Concise Explanation.
"Comparison of enhancement index of radial artery in patients with different glucose tolerance and influencing factors analysis thereof"; with English Abstract and partial English Translation of the Chinese Office Action issued on Oct. 30, 2019 as a concise explanation of the relevance.

* cited by examiner

ELECTRONIC DEVICE FOR DETECTING A PULSE WAVE OF A SUBJECT

CROSS REFERENCE TO RELATED APPLICATION

This application claims priority to and the benefit of Japanese Patent Application No. 2015-109500 (filed on May 29, 2015), the entire contents of which are incorporated herein by reference.

TECHNICAL FIELD

This disclosure relates to an electronic device for estimating a state of health of a subject from measured biological information.

BACKGROUND

Conventionally, measurement of blood components and blood fluidity have been conducted as a means for estimating a state of health of a subject (user). Such measurements use blood collected from the subject. Electronic devices for measuring biological information from a wrist or other measured part of a subject are also known. For example, an electronic device that measures a subject's pulse when worn on the subject's wrist is known.

SUMMARY

An electronic device according to the disclosure includes:
a wearing portion to be worn by a subject; and
a sensor unit including a sensor configured to detect a pulse wave of the subject,
wherein the sensor unit includes a displacement portion configured to contact a measured part of the subject and to be displaced in accordance with the pulse wave of the subject when the wearing portion is worn by the subject.

DETAILED DESCRIPTION

The pain involved in collecting blood prevents subjects from estimating their state of health on a routine basis. Also, a conventionally known electronic device described simply measures the pulse and, other than pulse, is unable to estimate the state of health of the subject.

In light of these considerations, it would be helpful to provide an electronic device that is capable of estimating the state of health of a subject in a simple and non-invasive manner.

Hereinafter, embodiments of the disclosure will be described in detail with reference to the accompanying drawings.

First Embodiment

Figure 1:
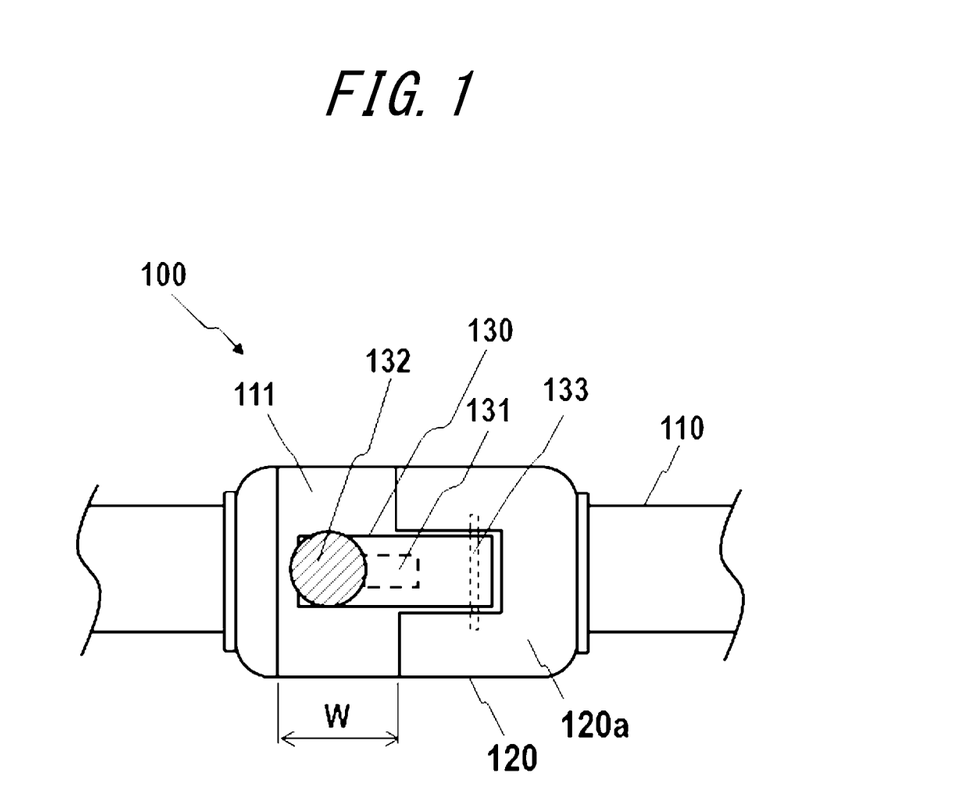
FIG. 1 is a schematic diagram illustrating a configuration of an electronic device according to a first embodiment.

FIG. 1 is a schematic diagram illustrating a configuration of an electronic device according to a first embodiment. The electronic device 100 includes a wearing portion 110 and a measurement unit 120. FIG. 1 is a view of the electronic device 100 from a rear face 120a which comes into contact with a measured part.

The electronic device 100 measures biological information of a subject when the electronic device is being worn by the subject. The biological information measured by the electronic device 100 is the subject's pulse wave that is measurable by the measurement unit 120. According to the present embodiment, the electronic device 100 is described below as being worn on, for example, the wrist of the subject to acquire the pulse wave.

According to the present embodiment, the wearing portion 110 is an elongated strip-like straight band. Measurement of the pulse wave is preformed when, for example, in a state where the subject has wrapped the wearing portion 110 of the electronic device 100 around the wrist. In particular, the subject wraps the wearing portion 110 around the wrist in such a manner that the rear face 120a of the measurement unit 120 contacts the measured part for measurement of the pulse wave. The electronic device 100 measures the pulse wave of blood flowing through the ulnar artery or the radial artery at the subject's wrist.

Figure 2:
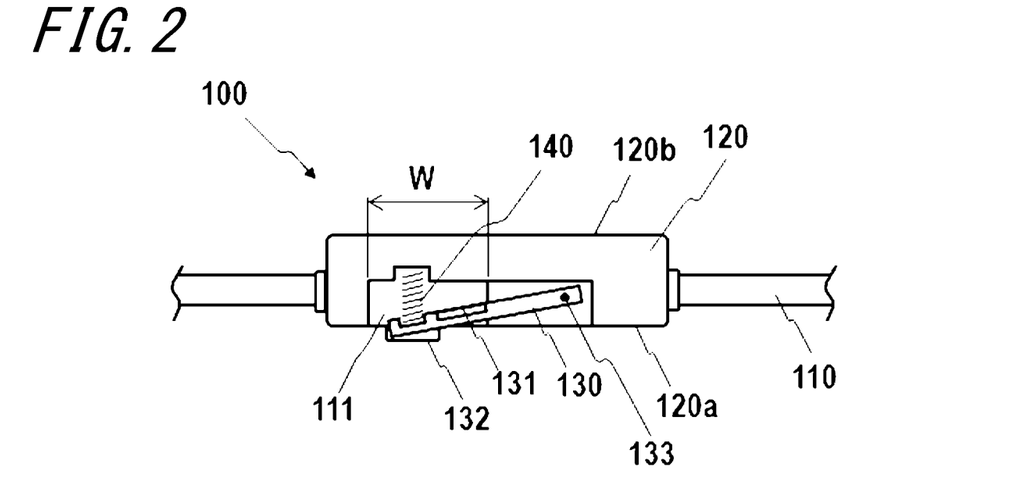
FIG. 2 is a cross-sectional diagram schematically illustrating a configuration of a main section of FIG. 1.

FIG. 2 is a cross-sectional diagram schematically illustrating the configuration of the measurement unit 120 of FIG. 1. FIG. 2 illustrates, together with the measurement unit 120, the wearing portion 110 in the vicinity thereof.

The measurement unit 120 includes the rear face 120a which contacts the subject's wrist when the subject is wearing the electronic device 100, and a front face 120b on an opposite side from the rear face 120a. The measurement unit 120 includes an opening 111 formed on the rear face 120a. In a state where an elastic body 140 is not compressed, a sensor unit 130 has one end protruding to the rear face 120a through the opening 111 and is supported by the measurement unit 120. The one end of the sensor unit 130 is provided with a pulse contact portion 132. The one end of the sensor unit 130 is displaceable in a direction substantially perpendicular to the plane of the rear face 120a. The other end of the sensor unit 130 is supported by the measuring unit 120 via a supported portion 133 in such a manner as to allow displacement of the one end of the sensor unit 130.

The one end of the sensor unit 130 is in contact with the measurement unit 120 via the elastic body 140 and is displaceable. The elastic body 140 is, for example, a spring. However, the elastic body 140 is not limited to being a spring and can be any other elastic body such as a resin or a sponge.

Although not illustrated, the measurement unit 120 may be provided with a controller, a memory, a communication interface, a power source, a notification interface, together with a circuit for operating these elements, a cable for connecting these elements, and the like.

The sensor unit 130 includes an angular velocity sensor 131 configured to detect displacement of the sensor unit 130. The angular velocity sensor 131 needs to simply detect angular displacement of the sensor unit 130. The sensor provided to the sensor unit 130 is not limited to an angular velocity sensor 131 and may include, for example, an acceleration sensor, an angle sensor, other motion sensors, or any combination thereof.

Figure 3:
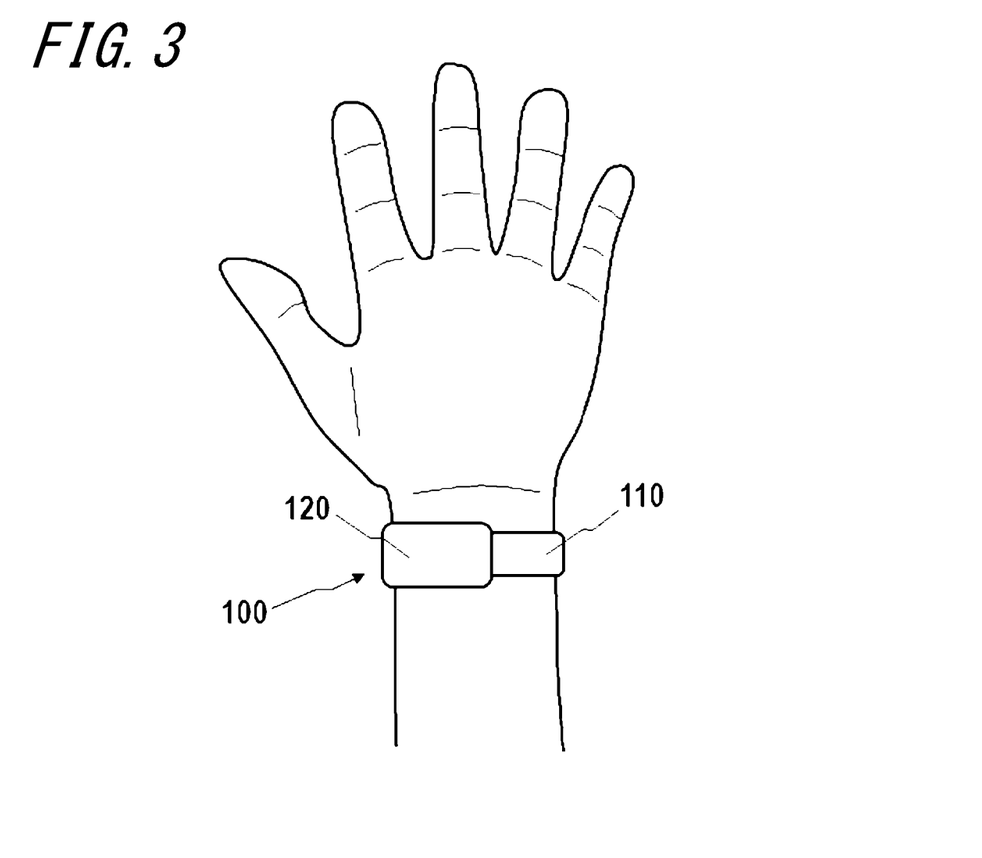
FIG. 3 is a diagram illustrating an example of a using condition of the electronic device of FIG. 1.

FIG. 3 illustrates an example of a state in which the electronic device 100 is being used by the subject. For use, the subject wears the electronic device 100 around the wrist. The electronic device 100 is worn in such a manner that the rear face 120a of the measurement unit 120 comes into contact with the measured part. In a state where the wearing portion 110 is wrapped around the wrist, a position of the measurement unit 120 may be adjusted such that the pulse contact unit 132 is in contact with a position corresponding to the ulnar artery or the radial artery.

In FIG. 3, in a state where the electronic device 100 is worn by the subject, the one end of the sensor unit 130 contacts the skin over the radial artery, which is the artery positioned close to the thumb of the left hand of the subject. Due to the elastic force applied by the elastic body 140 disposed between the measurement unit 120 and the sensor unit 130, the one end of the sensor unit 130 contacts the skin above the radial artery of the subject. The sensor unit 130 is displaced in accordance with movement of the subject's radial artery, i.e., pulsation. The angular velocity sensor 131 obtains a pulse wave by detecting the displacement of the sensor unit 130. The pulse wave is expressed as a waveform representing changes in a volume of the blood vessel over time caused by inflow of blood and acquired from the body surface.

Referring back to FIG. 2, in a state where the elastic body 140 is not being compressed, the one end of the sensor unit 130 protrudes from the opening 111. When the subject is wearing the electronic device 100, the one end of the sensor unit 130 is in contact with the skin above the subject's radial artery. In this state, the elastic body 140 extends and contracts in accordance with the pulsation, causing displacement of the one end of the sensor unit 130. The elastic body 140 is a material with an appropriate elastic modulus so as to enable extension and contraction in accordance with the pulsation, in a manner which does not inhibit the pulsation. An opening width W of the opening 111 should be sufficiently wider than a diameter of the blood vessel, i.e., the radial artery according to the present embodiment. The opening 111 of the measurement unit 120 prevents the rear face 120a of the measurement unit 120 from pressing the radial artery when the electronic device 100 is being worn. This enables the electronic device 100 to acquire the pulse wave with less noise, thus improving measurement accuracy.

FIG. 3 illustrates an example in which the electronic device 10 is worn on the wrist and acquires the pulse wave from the radial artery. However, the disclosure is not limited to this example. For example, the electronic device 100 may acquire the pulse wave from the blood flowing in the carotid artery in the subject's neck. In particular, the subject may measure the pulse wave by lightly pressing the pulse contacting unit 132 against a position corresponding to the carotid artery. Alternatively, the subject may wrap the wearing portion 110 around the neck such that the pulse contact portion 132 is positioned above the carotid artery.

Figure 4:
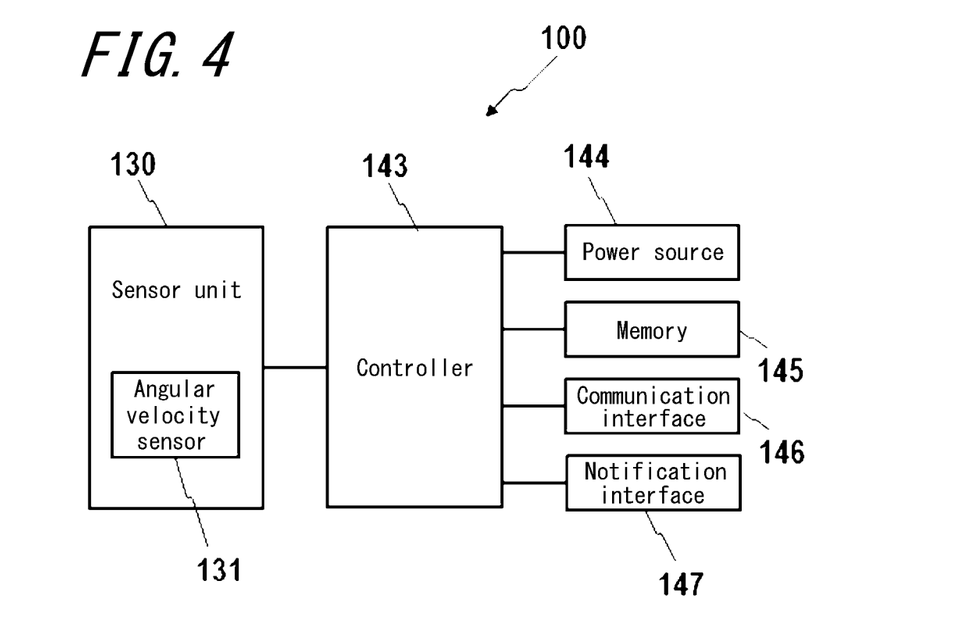
FIG. 4 is a functional block diagram illustrating a configuration of the electronic device of FIG. 1.

FIG. 4 is a functional block diagram illustrating a configuration of the electronic device 100. The electronic device 100 includes the sensor unit 130, a controller 143, a power source 144, a memory 145, a communication interface 146, and a notification interface 147. According to the present embodiment, the controller 143, the power source 144, the memory 145, the communication interface 146, and the notification interface 147 are accommodated in the measurement unit 120 or the wearing portion 110.

The sensor unit 130 includes the angular velocity sensor 131 and acquires the pulse wave by detecting pulsation from the measured part.

The controller 143 is a processor for overall control and management of the electronic device 100, including, for example, each functional block of the electronic device 100. Furthermore, the controller 143 is a processor configured to calculate an index on the basis of a pulse wave propagation phenomenon from the acquired pulse wave. The controller 143 is configured with a processor such as CPU (Central Processing Unit) to execute a program that defines control procedures and a program for calculation of the index on the basis of the pulse wave propagation phenomenon. These programs are stored in a storage medium such as the memory 145. Also, the controller 143 estimates a state related to subject's glucose metabolism, lipid metabolism, or the like, on the basis of the calculated index. The controller 143 provides data to the notification interface 147.

The power source 144 includes, for example, a lithium ion battery and a control circuit for charging and discharging the lithium ion battery, and supplies power to the electronic device 100 overall.

The memory 145 stores programs and data. The memory 145 may include any non-transitory storage medium such as a semiconductor storage medium and a magnetic storage medium. The memory 145 may include a plurality of types of the storage media. The memory 145 may include a combination of a portable storage medium such as a memory card, an optical disk, and a magneto-optical disk, and an apparatus for reading the storage medium. The memory 145 may include a storage device such as RAM (Random Access Memory) for use as a temporary storage area. The memory 145 stores various information and programs for operating the electronic device 100 and, simultaneously, functions as a working memory. The memory 145 may store, for example, a measurement result of the pulse wave acquired by the sensor unit 130.

The communication interface 146 transmits and receives various data through wired or wireless communication with an external device. For example, the communication interface 146 communicates with an external device that stores the biological information of the subject for the purpose of managing a state of health, and transmits the measurement result of the pulse wave measured by the electronic device 100 and the state of health estimated by the electronic device 100 to the external device.

The notification interface 147 provides notification of information by sound, vibration, images, and so on. The notification interface 147 may include a speaker, a vibrator, or a display device such as a Liquid Crystal Display (LCD), an Organic Electro-Luminescence Display (OELD), or an Inorganic Electro-Luminescence Display. (IELD) According to the present embodiment, the notification interface 147 provides notification of, for example, the state of the subject's glucose metabolism or lipid metabolism.

Figure 5:
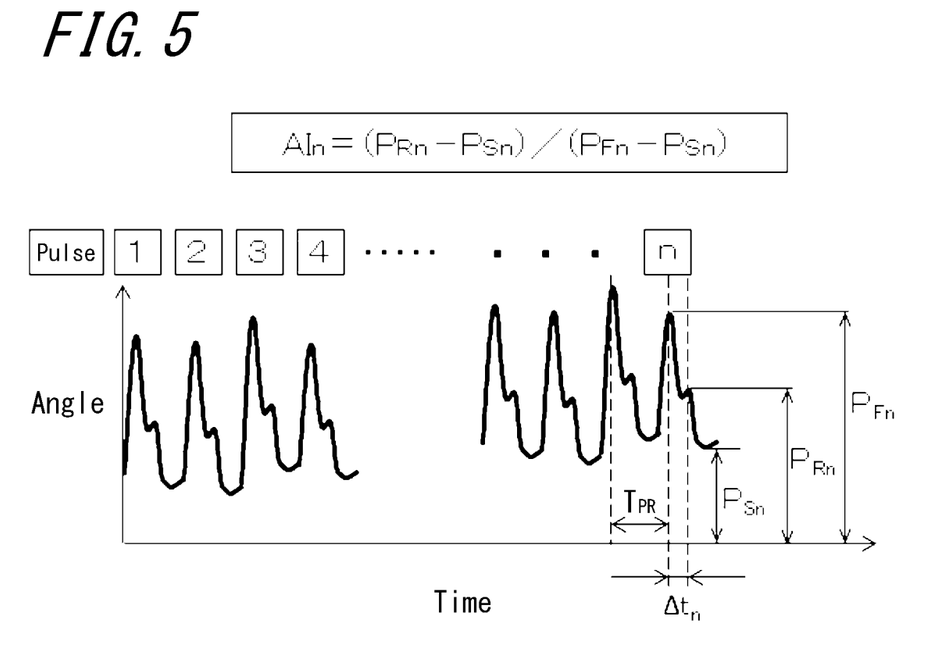
FIG. 5 is a graph illustrating an example of a pulse wave obtained by a sensor unit.

FIG. 5 is a graph illustrating an example of the pulse wave acquired from the wrist using the electronic device 100. FIG. 5 illustrates the case where the angular velocity sensor 131 is used as the means for detecting the pulsation. In FIG. 5, an angular velocity obtained by the angular velocity sensor 131 is time-integrated, with the horizontal axis and the vertical axis representing time and angle, respectively. Since the acquired pulse wave may, for example, include noise caused by movement of the subject's body, the pulse wave may be corrected using a filter that removes Direct Current (DC) components, so as to extract only the pulsation component.

A method of calculating a pulse wave index from the acquired pulse wave will be described with reference to FIG. 5. Pulse wave propagation is a phenomenon in which pulsation caused by blood being pumped from the heart is transmitted through the arterial wall and the blood. The pulsation transmitted by the blood pumped from the heart reaches peripheral sites of the hands and the feet as a forward wave, a portion of which is reflected at locations such as where a blood vessel branches, or where the diameter of a blood vessel changes, and returns as a reflected wave. The pulse wave index may be, for example, a Pulse Wave Velocity (PWV) of the forward wave, a magnitude $P_R$ of the reflected wave of the pulse wave, a time difference $\Delta t$ between the forward wave and the reflected wave of the pulse wave, or an Augmentation Index (AI) representing a ratio of the magnitude of the forward wave to the magnitude of the reflected wave.

The pulse wave illustrated in FIG. 5 indicates n beats of the user's pulse, where n is an integer of at least 1. The pulse wave is a combined wave in which the forward wave caused by the blood pumped out of the heart overlaps with the reflected wave caused by branches of the blood vessel or portions where the diameter of the blood vessel changes. In FIG. 5, $P_{Fn}$ represents the magnitude of a peak of the pulse wave caused by the forward wave of each pulse, and $P_{Rn}$ represents the magnitude of a peak of the pulse wave caused by the reflected wave of each pulse. $P_{Sn}$ represents a minimum value of the pulse wave of each pulse. In FIG. 5, also, $T_{PR}$ represents an interval between the peaks of the pulses.

The pulse wave index quantifies information obtained from the pulse wave. An example of a pulse wave index is PWV, which is calculated using a difference in propagation time of pulse waves measured at two measured parts such as the upper arm and the ankle, and a distance therebetween. In particular, the PWV is calculated by synchronously acquiring pulse waves at two points of an artery (e.g., at the upper arm and the ankle) and dividing the distance (L) between the two points by a time difference (PTT) of the pulse waves at the two points. A further example of the pulse wave index is the magnitude $P_R$ of the reflected wave, which may be calculated as the magnitude $P_{Rn}$ of the peak of the pulse wave caused by the reflected wave or a mean value $P_{Rave}$ of the n values of $P_{Rn}$. A further example of a pulse wave index is the time difference $\Delta t$ between the forward wave and the reflected wave of the pulse wave, which may be calculated as the time difference $\Delta tn$ of a given pulse or a mean value $\Delta t_{ave}$ of the n values of $\Delta tn$. A further example of a pulse wave index is the AI, which is obtained by dividing the magnitude of the reflected wave by the magnitude of the forward wave and expressed as $AI_n=(P_{Rn}-P_{Sn})/(P_{Fn}-P_{Sn})$. $AI_n$ represents the AI of each pulse wave. As a pulse wave index, AI may, for example be obtained by measuring the pulse wave for several seconds and calculating a mean value $AI_{ave}$ of the $AI_n$ (n is an integer of at least 1) of each pulse.

The PWV, the magnitude $P_R$ of the reflected wave, the time difference $\Delta t$ between the forward wave and reflected wave, and the AI vary depending on hardness of the blood vessel wall and thus may be used for estimation of a state of arteriosclerosis. For example, when the vessel wall is hard, the pulse wave velocity PWV increases. For example, when the vessel wall is hard, the magnitude $P_R$ of the reflected wave increases. For example, when the vessel wall is hard, the time difference $\Delta t$ between the forward wave and the reflected wave decreases. For example, when the vessel wall is hard, the AI increases. Further, by using these pulse wave indices as described above, the electronic device 100 may estimate the state of arteriosclerosis and the blood fluidity (viscosity). In particular, the electronic device 100 may estimate a change in the blood fluidity from a change in the pulse wave index acquired at the same measured part of the same subject during a time period over which there is substantially no change in the state of arteriosclerosis (e.g. within a few days). Here, the blood fluidity indicates a degree of ease of the blood flow. For example, when the blood fluidity is low, the pulse wave velocity PWV decreases. For example, when the blood fluidity is low, the magnitude $P_R$ of the pulse wave decreases. For example, when the blood fluidity is low, the time difference $\Delta t$ between the forward wave and the reflected wave increases. For example, when the blood fluidity is low, the AI decreases.

According to the present embodiment, the electronic device 100 calculates, by way of example, the pulse wave velocity (PWV), the magnitude $P_R$ of the reflected wave, the time difference $\Delta t$ between the forward wave and the reflected wave, or the AI as the pulse wave index. However, the pulse wave index is not limited thereto. For example, the electronic device 100 may use a posterior systolic blood pressure as the pulse wave index.

Figure 6:
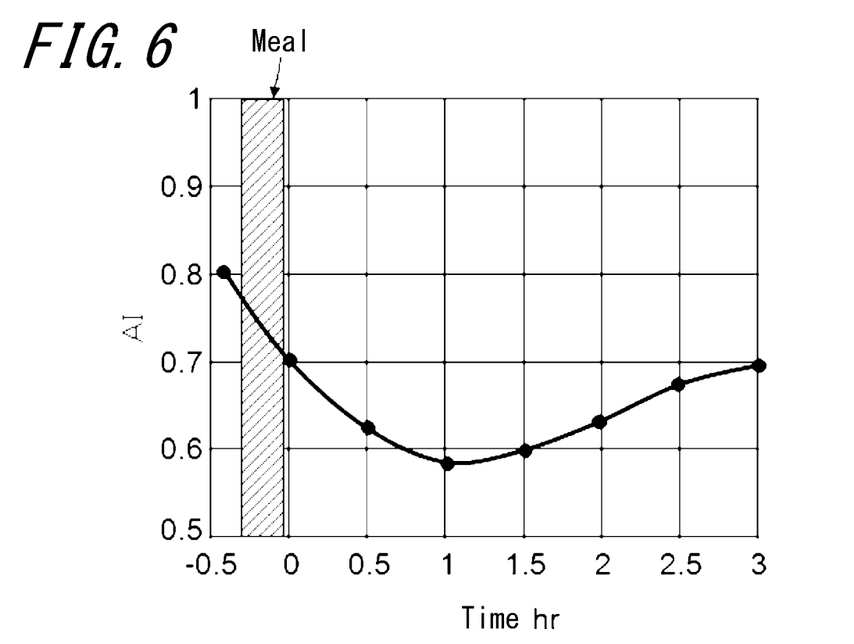
FIG. 6 is a graph illustrating changes in a calculated AI over time.

FIG. 6 is a graph illustrating changes in the calculated AI over time. According to the present embodiment, the pulse wave was acquired for approximately 5 seconds by the electronic device 100 equipped with the angular velocity sensor 131. The controller 143 calculated the AI of each pulse from the obtained pulse wave and further calculated a mean value $AI_{ave}$ of the AI. According to the present embodiment, the electronic device 100 acquired the pulse wave at a plurality of timings before and after a meal and calculated the mean value of the AI (simply "AI" below) as one example of the pulse wave index. In FIG. 6, the horizontal axis indicates elapsed time, with a first measurement time after the meal set as 0. In FIG. 6, the vertical axis indicates the AI calculated from the pulse wave acquired at the corresponding time. The pulse wave was acquired above the radial artery while the subject was resting.

The electronic device 100 acquired the pulse wave before the meal, immediately after the meal, and every 30 minutes after the meal, and calculated a plurality of AI based on the pulse wave at each time. The AI calculated from the pulse wave obtained before the meal was approximately 0.8. As compared with the AI before the meal, the AI immediately after the meal was smaller, and the AI reached its lowest value approximately 1 hour after the meal. Then, the AI gradually increased in the three hours after the meal, until the completion of the measurement.

The electronic device 100 can estimate the change in the blood fluidity from the change in the calculated AI. For example, the blood fluidity becomes low when the red blood cells, the white blood cells, and the platelets are solidified, or when the adhesiveness increases. For example, the blood fluidity also becomes low when the plasma content in the blood decreases. The blood fluidity changes depending on the state of health of the subject such as states of the glucose metabolism and the lipid metabolism described below, heat stroke, dehydration, hypothermia, and the like. The electronic device 100 according to the present embodiment enables the subject to know a change in his/her blood fluidity before the state of health of the subject becomes severe. From the changes in AI before and after the meal as illustrated in FIG. 6, it can be inferred that the blood fluidity becomes low after a meal, reaching a minimum approximately 1 hour after the meal, and then gradually increasing thereafter. The electronic device 100 may issue a notification indicating a low blood fluidity state as "thick" or a high blood fluidity state as "thin". For example, the electronic device 100 may make the determination of "thick" or "thin" on the basis of the mean value of the AI for the subject's actual age as a standard. The electronic device 100 may make the determination of "thin" when the calculated AI is greater than the mean value, or "thick" when the calculated AI is less than the mean value. For example, the electronic device 100 may determine whether "thick" or "thin" based on the AI before the meal. The electronic device 100 may determine a degree of "thickness" by comparing the AI after the meal with the AI before the meal. The electronic device 100 may use, for example, the AI before the meal, i.e., the AI with empty stomach as a reference for the subject's vascular age (the hardness of the blood vessel). The electronic device 100, by calculating an amount of change of the calculated AI with respect to the AI of the subject before the meal, i.e., the AI with empty stomach, may reduce an estimation error due to the subject's vascular age (the hardness of the blood vessel). In this way, the electronic device 100 may more accurately estimate the change in the blood fluidity.

Figure 7:
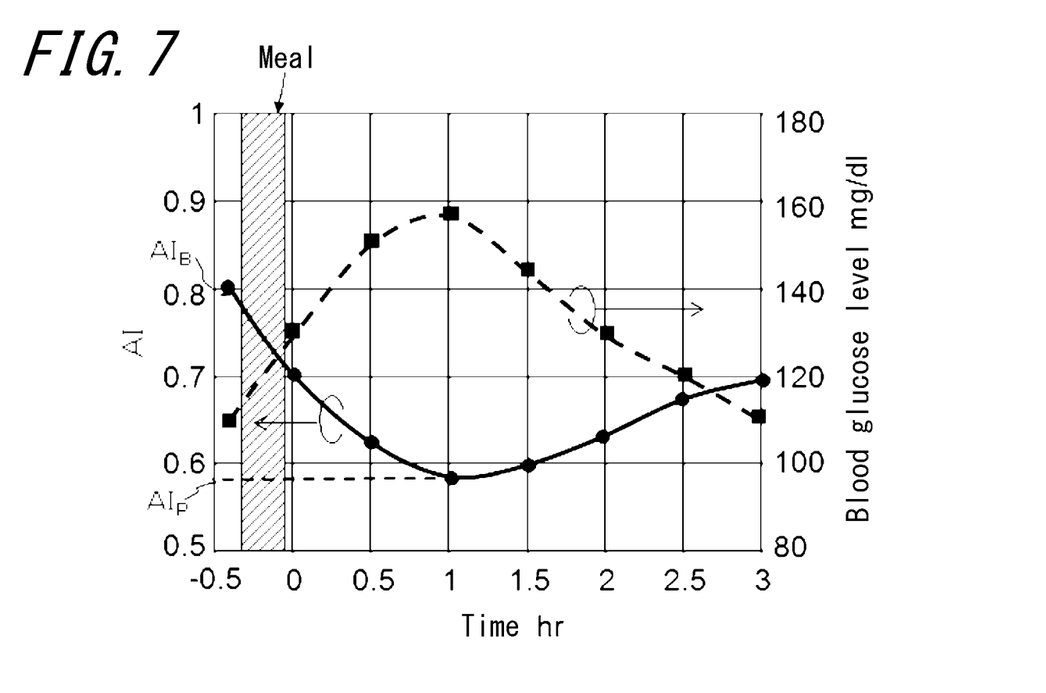
FIG. 7 is a graph illustrating the calculated AI and measurement results of a blood glucose level.

FIG. 7 is a graph illustrating the calculated AI and measurement results of a blood glucose level. The method for acquiring the pulse wave and the method for calculating the AI are similar to those of the embodiment illustrated in FIG. 6. In FIG. 7, the vertical axis on the right side represents the blood glucose level, and the vertical axis on the left side represents the calculated AI. In FIG. 7, a solid line represents the AI calculated from the acquired pulse wave, and a broken line represents a measured blood glucose level. The blood glucose level was measured immediately after the pulse wave was acquired. The blood glucose level was measured using the "Medi-Safe Fit" blood glucose measurement device produced by TERUMO CORPORATION. As compared with the blood glucose level before the meal, the blood glucose level immediately after the meal increased by approximately 20 mg/dl. The blood glucose level reached a maximum at approximately 1 hour after the meal. Then, the blood glucose level gradually decreased until the measurement was completed and, at approximately 3 hours after the meal, became substantially equal to the blood glucose level before the meal.

As illustrated in FIG. 7, the blood glucose levels before and after the meal are negatively correlated with the AI calculated from the pulse wave. When the blood glucose level is high, sugar in the blood causes a mass of the red blood cells and the platelets, or increases the viscosity of the blood. As a result, the blood fluidity may decrease. The decrease in the blood fluidity may reduce the pulse wave velocity PWV. The decrease in the pulse wave velocity PWV may cause an increase in the time difference Δt between the forward wave and the reflected wave. The increase in the time difference Δt between the forward wave and the reflected wave may cause a decrease in the magnitude $P_R$ of the reflected wave with respect to the magnitude $P_F$ of the forward wave. The decrease in the magnitude $P_R$ of the reflected wave with respect to the magnitude $P_F$ of the forward wave may cause a decrease in the AI. The AI within several hours after the meal (3 hours according to the present embodiment) has a correlation with the blood glucose level. Therefore, a change in the blood glucose level of the subject may be inferred from the change in the AI. Also, by measuring the blood glucose level of the subject in advance and obtaining a correlation thereof with the AI, the electronic device 100 may estimate the blood glucose level of the subject based on the calculated AI.

The electronic device 100 may estimate a state of the subject's glucose metabolism on the basis of the time at which $AI_P$, which represents a first detected minimum extreme value of the AI after the meal. The electronic device 100 estimates, for example, the blood glucose level indicative of the state of the glucose metabolism. As an example of estimating the state of the glucose metabolism, the electronic device 100 may infer that the subject has glucose metabolism disorder (the subject is a diabetic) when, for example, a first detected minimum extreme value $AI_P$ of the AI after the meal is detected after a predetermined time period (e.g., approximately 1.5 hours from the meal) or longer.

The electronic device 100 may estimate the state of the subject's glucose metabolism on the basis of a difference $(AI_B - AI_P)$ between $AI_B$ representing the AI before the meal and the first detected minimum extreme value $AI_P$ of the AI after the meal. As an example of estimating the state of the glucose metabolism, the electronic device 100 may infer that the subject has glucose metabolism disorder (the subject is a postprandial hyperglycemia patient) when $(AI_B - AI_P)$ is greater than or equal to a predetermined value (e.g., 0.5 or higher).

Figure 8:
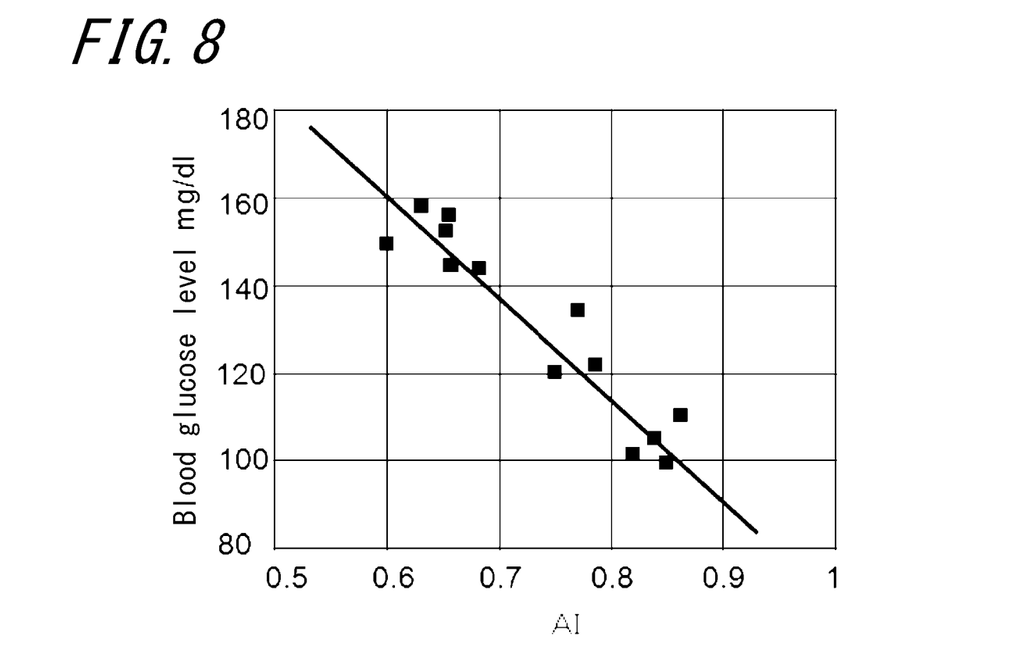
FIG. 8 is a graph illustrating a relation between the calculated AI and the blood glucose level.

FIG. 8 is a graph illustrating a relationship between the calculated AI and the blood glucose level. The calculated AI and the blood glucose level were acquired within 1 hour after a meal, when the blood glucose level varies greatly. The data of FIG. 8 include a plurality of different data points of the same subject after the meal. As illustrated in FIG. 8, the calculated AI and the blood glucose level are negatively correlated. The correlation coefficient of the calculated AI and the blood glucose level is at least 0.9, indicating high correlation. For example, by acquiring the correlation of the calculated AI and the blood glucose level as illustrated in FIG. 8 from each subject in advance, the electronic device 100 may estimate the subject's blood glucose level from the calculated AI.

Figure 9:
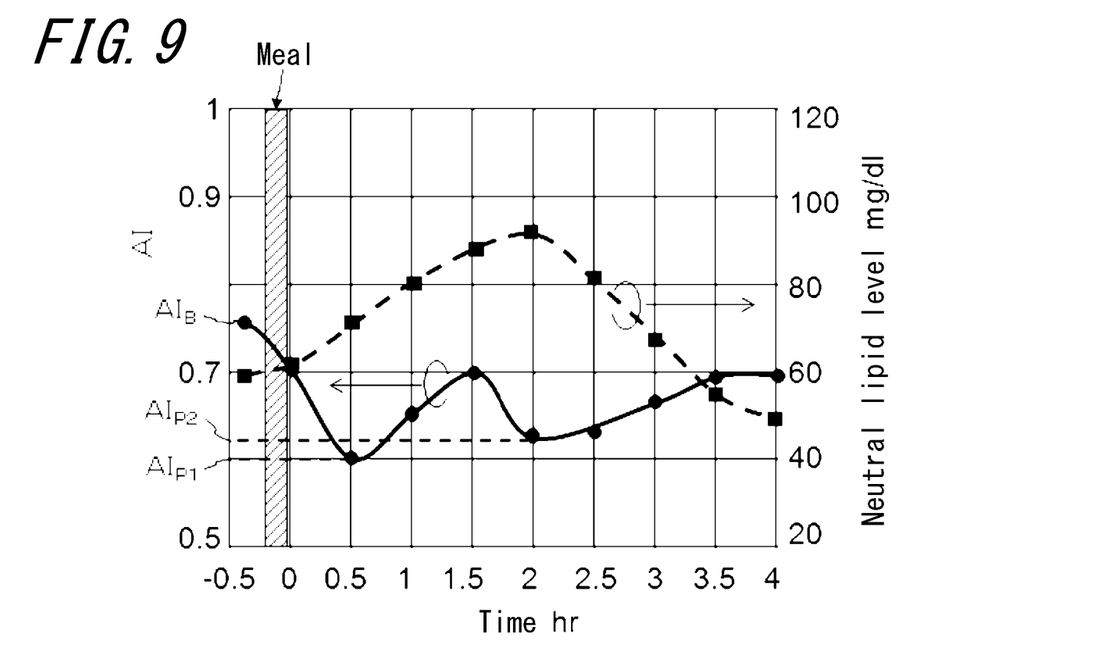
FIG. 9 is a graph illustrating the calculated AI and measurement results of a triglyceride level.

FIG. 9 is a graph illustrating the calculated AI and measurement results of a neutral lipid level. The method for acquiring the pulse wave and the method for calculating the AI are the same as those of the embodiment illustrated in FIG. 6. In FIG. 9, the vertical axis on the right side represents the neutral lipid level in the blood, and the vertical axis on the left side indicates the AI. In FIG. 9, a solid line represents the AI calculated from the obtained pulse wave, and a broken line represents a measured triglyceride level. The neutral lipid level was measured immediately after the pulse wave was acquired. The neutral lipid level was measured using the "Pocket Lipid" lipid measuring device produced by Techno Medica Co., Ltd. As compared with the neutral lipid level before the meal, the maximum extreme value of the neutral lipid level after the meal rose by approximately 30 mg/dl. The neutral lipid level reached the maximum extreme value at approximately 2 hours after the meal. Subsequently, the neutral lipid level gradually decreased until the measurement was completed and, at approximately 3.5 hours after the meal, became substantially equal to the neutral lipid level before the meal.

In contrast, the minimum extreme values of the calculated AI were a first minimum extreme value $AI_{P1}$ detected at approximately 30 minutes after the meal, and a second minimum extreme value $AI_{P2}$ detected at approximately 2 hours after the meal. It can be inferred that the first minimum extreme value $AI_{P1}$ detected at approximately 30 minutes after the meal was caused by the influence of the blood glucose level after the meal as described above. The second minimum extreme value $AI_{P2}$ detected at approximately 2 hours after the meal is substantially coincident with the maximum extreme value of the neutral lipid level detected at approximately 2 hours after the meal. From this, it can be inferred that the second minimum extreme value $AI_{P2}$ detected after a predetermined time period from the meal is due to the effect of the neutral lipids. It can be understood that the neutral lipid levels before and after the meal, similarly to the blood glucose level, have a negative correlation with the AI calculated from the pulse wave. In particular, the minimum extreme value $AI_{P2}$ of the AI detected after the predetermined time period (after 1.5 hours according to the present embodiment) from the meal is correlated with the neutral lipid level. Therefore, the change in the subject's neutral lipid level can be estimated from the change in the AI. Also, by measuring the subject's neutral lipid level in advance and determining a correlation with the AI, the electronic device 100 may estimate the neutral lipid level of the subject from the calculated AI.

The electronic device 100 can estimate the state of the subject's lipid metabolism on the basis of the time at which the second minimum extreme value $AI_{P2}$ is detected after the predetermined time from the meal. The electronic device 100 estimates, for example, a lipid level as the state of the lipid metabolism. As an example, the electronic device 100 may infer that the subject has abnormal lipid metabolism (the subject is a hyperlipidemia patient) when the second minimum extreme value $AI_{P2}$ is detected after the predetermined time or longer (e.g., more than 4 hours) from the meal.

The electronic device 100 can estimate the state of the subject's lipid metabolism on the basis of a difference $(AI_B - AI_{P2})$ between $AI_B$ representing the AI before the meal and the second minimum extreme value $AI_{P2}$ detected after the predetermined time period from the meal. As an example, the electronic device can infer that the subject's lipid metabolism is abnormal (the subject is a postprandial hyperlipidemia patient), when, for example, the difference $(AI_B - AI_{P2})$ is equal to or greater than 0.5.

Also, from the measurement results illustrated in FIG. 7 to FIG. 9, the electronic device 100 according to the present embodiment may estimate the state of the subject's glucose metabolism on the basis of the first minimum extreme value $AI_{P1}$, detected earliest after the meal, and the occurrence time thereof. Further, the electronic device 100 according to the present embodiment can estimate the state of the subject's lipid metabolism on the basis of the second minimum extreme value $AI_{P2}$, detected after the predetermined time period from the detection of the first minimum extreme value $AI_{P1}$, and the occurrence time thereof.

Although, according to the present embodiment, the neutral lipid level is acquired for the estimation of the lipid metabolism, the estimation of the lipid metabolism is not limited thereto. The lipid level estimated by the electronic device 100 includes, for example, total cholesterol level, High Density Lipoprotein (HDL) cholesterol level, Low Density Lipoprotein (LDL) cholesterol level, and so on. These lipid levels exhibit tendencies similar to the above described case of neutral lipids.

Figure 10:
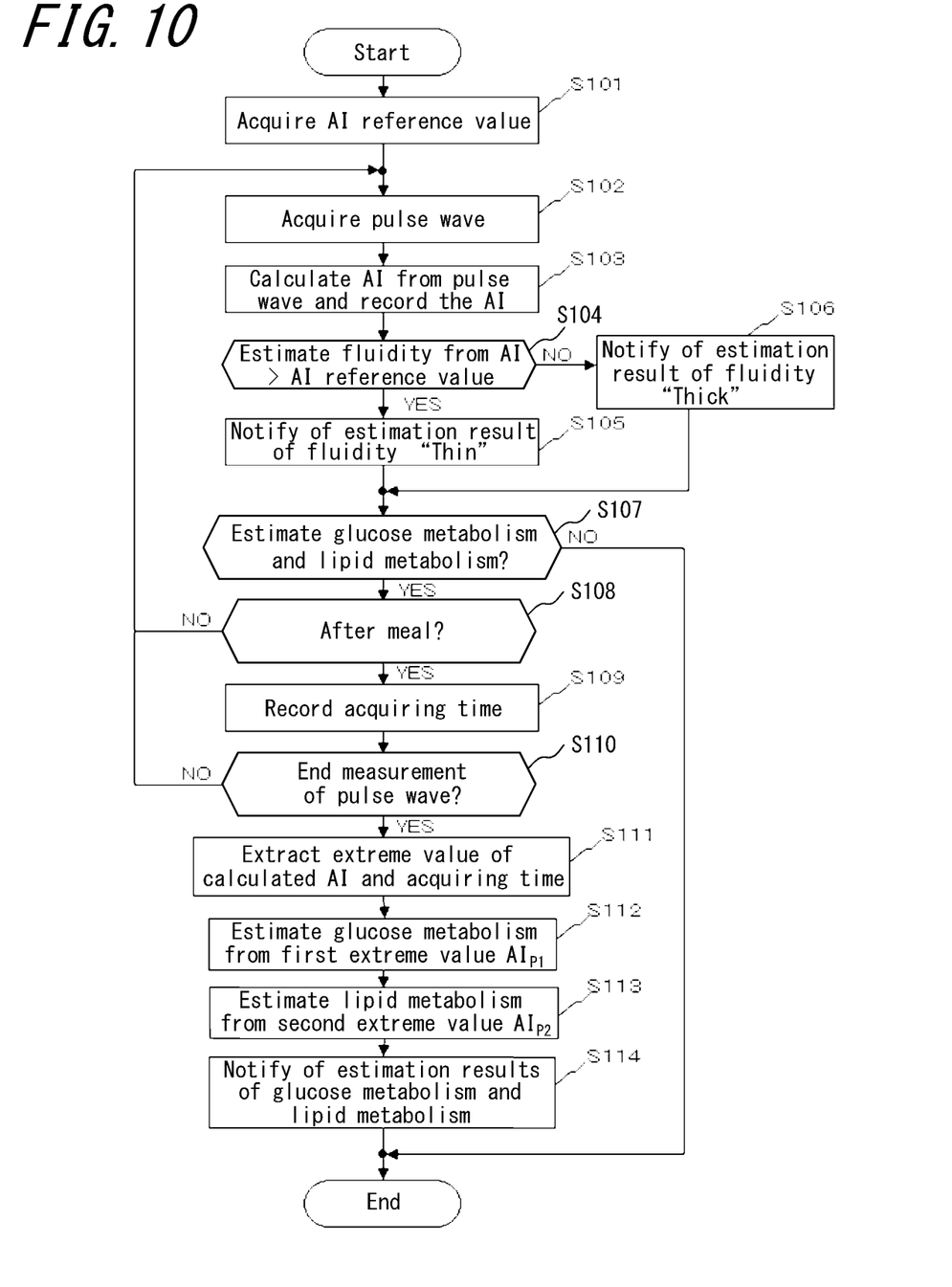
FIG. 10 is a flowchart illustrating procedure to estimate blood fluidity, glucose metabolism, and lipid metabolism.

FIG. 10 is a flowchart illustrating a process for estimating the blood fluidity and the states of the glucose metabolism and the lipid metabolism on the basis of the AI. Referring to FIG. 10, the process by which the electronic device 100 according to the present embodiment estimates the blood fluidity and the states of the glucose metabolism and the lipid metabolism based on the AI will be described.

As illustrated in FIG. 10, the electronic device 100 acquires an AI reference value of the subject as an initial setting (step S101). The AI reference value may be an average AI estimated from the subject's age or the AI acquired in advance from the subject with an empty stomach. The electronic device 100 may also use the AI determined to be before the meal in steps S102 to S108 or the AI calculated immediately before the measurement of the pulse wave as the AI reference value. In this case, the electronic device 100 executes step S101 after steps S102 to S108.

Subsequently, the electronic device 100 acquires the pulse wave (step S102). For example, the electronic device 100 determines whether a pulse wave with at least a predetermined amplitude is obtained in a predetermined measurement time (e.g., 5 seconds). When a pulse wave with at least the predetermined amplitude is acquired, the electronic device 100 proceeds to step S103. When a pulse wave with at least the predetermined amplitude is not acquired, the electronic device 100 repeats step S102 (these steps are not illustrated). At step S102, upon detection of, for example, a pulse wave with at least the predetermined amplitude, the electronic device 100 autonomously acquires the pulse wave.

The electronic device 100 calculates the AI serving as the pulse wave index from the pulse wave obtained at step S102 and stores the calculated AI in the memory 34 (step S103). The electronic device 100 may obtain the AI by calculating the average $AI_{ave}$ from the $AI_n$ (n is an integer of 1 to n) of a predetermined number of pulses (e.g., 3 pulses). Alternatively, the electronic device 100 may calculate the AI of a specific pulse.

The AI may be calculated by performing a correction using, for example, a pulse rate PR, a pulse pressure $(P_F - P_S)$, body temperature, temperature of a detection part, and so on. It is known that there is a negative correlation between the pulse and the AI and between the pulse pressure and the AI, and also that there is a positive correlation between the temperature and the AI. When performing the correction, for example, the electronic device 100 calculates the pulse rate and the pulse pressure in addition to the AI at step S103. For example, the electronic device 100 may be equipped with a temperature sensor mounted on the sensor unit 130 to acquire temperature of the measured part when the pulse wave is obtained at step S102. The AI is corrected by substituting the obtained pulse rate, pulse pressure, and temperature into a correction equation prepared in advance.

Next, the electronic device 100 compares the AI reference value obtained at step S101 with the AI calculated at step S103 and estimates the blood fluidity of the subject (step S104). When the calculated AI is greater than the AI reference value (in the case of YES), the electronic device 100 determines that the blood fluidity is high and issues a notification such as "blood is thin" (step S105). When the calculated AI is not greater than the AI reference value (in the case of NO), the electronic device 100 determines that the blood fluidity is low and issues a notification such as "blood is thick" (step S106).

Next, the electronic device 100 confirms with the subject whether to estimate the states of the glucose metabolism and the lipid metabolism (step S107). When the states of the glucose metabolism and the lipid metabolism are not to be estimated at step S107 (in the case of NO), the electronic device 100 ends the process. When the states of the glucose metabolism and the lipid metabolism are to be estimated at step S107 (in the case of YES), the electronic device 100 confirms whether the calculated AI was acquired before or after the meal (step S108). When the calculated AI was not acquired after the meal (i.e., obtained before the meal) (in the case of NO), the electronic device 100 returns to step 5102 and acquires the next pulse wave. When the calculated AI was obtained after the meal (in the case of YES), the electronic device 100 stores the time at which the pulse wave corresponding to the calculated AI was acquired (step S109). Then, when the pulse wave is obtained (in the case of NO at step S110), the electronic device 100 returns step S102 and obtains the next pulse wave. To end the measurement of the pulse wave (in the case of YES at step S110), the electronic device 100 proceeds to step S111 and following steps to estimate the state of the subject's glucose metabolism and lipid metabolism.

Next, the electronic device 100 extracts the minimum extreme value and time corresponding thereto from a plurality of AI calculated at step S104 (step S111). For example, in the case of the AI indicated by the solid line in FIG. 9 being calculated, the electronic device 100 extracts the first minimum extreme value $AI_{P1}$ occurring at approximately 30 minutes after the meal and the second minimum extreme value $AI_{P2}$ occurring at approximately 2 hours after the meal.

Next, the electronic device 100 estimates the state of the subject's glucose metabolism from the first minimum extreme $AI_{P1}$ and the time corresponding thereto (step S112). Also, the electronic device 100 estimates the state of the subject's lipid metabolism from the second minimum extreme $AI_{P2}$ and the time corresponding thereto (step S113). Examples of the estimation of the states of the subject's glucose metabolism and lipid metabolism are similar to those of FIG. 9 and thus are omitted herein.

Next, the electronic device 100 notifies of the results of the estimation at steps S112 and S113 (step S114) and ends the process illustrated in FIG. 10. The notification interface 147 may issue a notification such as "normal glucose metabolism", "possible abnormal glucose metabolism", "normal lipid metabolism", "possible abnormal lipid metabolism". The notification interface 147 may issue advice such as "see a doctor", "improve your diet", and so on. Then, the electronic device 100 ends the process illustrated in FIG. 10.

According to the first embodiment as described above, the electronic device 100 can estimate the subject's blood fluidity and the states of the subject's glucose metabolism and lipid metabolism from the pulse wave index. Therefore, the electronic device 100 can estimate the subject's blood fluidity and the states of the subject's glucose metabolism and lipid metabolism in a quick and non-invasive manner.

According to the first embodiment as described above, the electronic device 100 can estimate the states of the subject's glucose metabolism and lipid metabolism from the extreme values of the pulse wave index and the time corresponding thereto. Therefore, the electronic device 100 can estimate the states of the subject's glucose metabolism and lipid metabolism in the quick and non-invasive manner.

According to the first embodiment as described above, the electronic device 100 can estimate the states of the subject's glucose metabolism and lipid metabolism using the pulse wave index before a meal (i.e., with the empty stomach) as a reference. Therefore, the electronic device 100 can accurately estimate the subject's blood fluidity and the states of the subject's glucose metabolism and lipid metabolism without regard to the blood vessel diameter, blood vessel hardness and so on, which do not exhibit short-term change.

According to the first embodiment as described above, preliminary calibration of the glucose level and the lipid level with respect to the index on the basis of the pulse wave enables the electronic device 100 to estimate the states of the subject's glucose metabolism and lipid metabolism in the quick and non-invasive manner.

Figure 11:
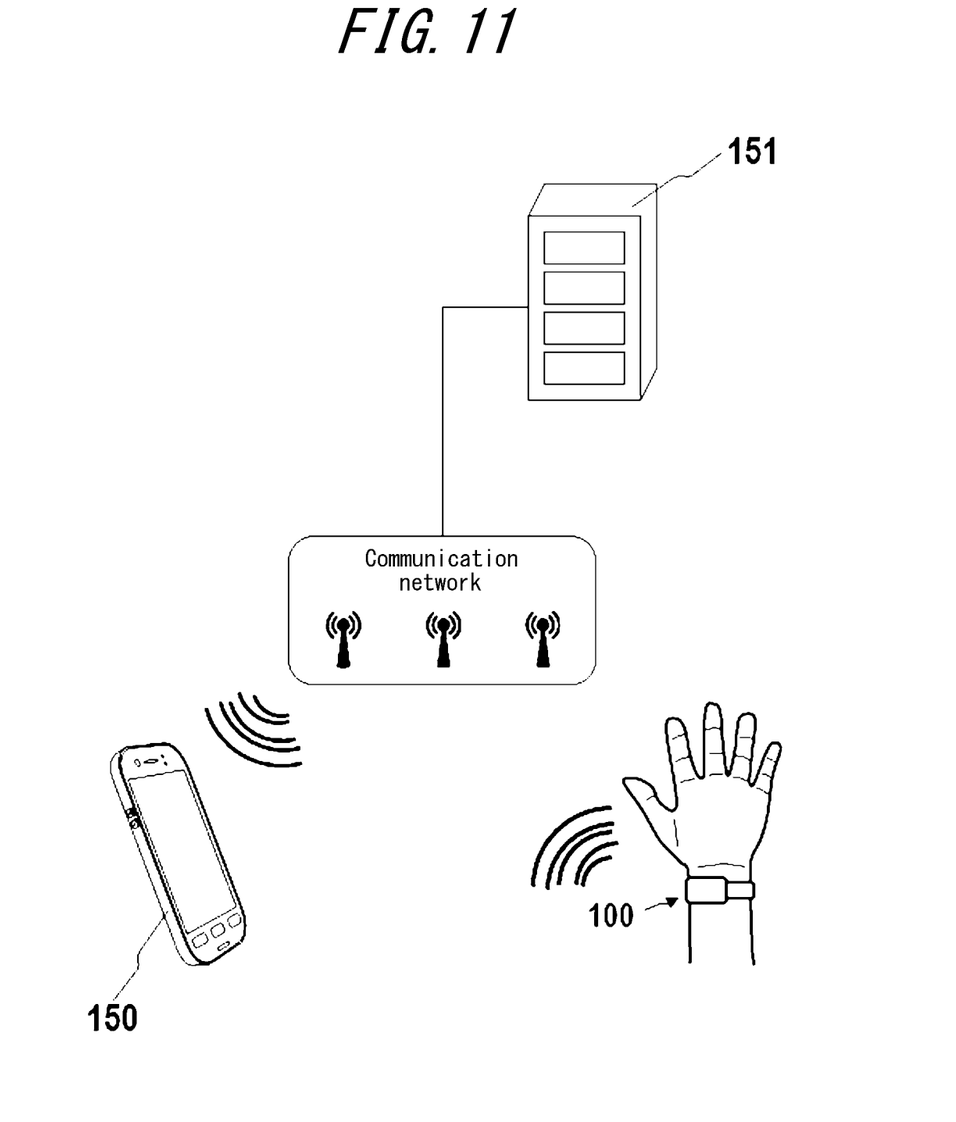
FIG. 11 is a schematic diagram illustrating a configuration of a system according to the first embodiment.

FIG. 11 is a schematic diagram illustrating a configuration of a system according to the first embodiment. The system according to the first embodiment illustrated in FIG. 11 includes the electronic device 100, a server 151, a mobile terminal 150, and a communication network. As illustrated in FIG. 11, the pulse wave index calculated by the electronic device 100 is transmitted to the server 151 via the communication network and stored, as personal information of the subject, in the server 151. The server 151, by comparing the index with information obtained from the subject in the past or various databases, estimates the subject's blood fluidity and the states of the subject's glucose metabolism and lipid metabolism. The server 151 also generates appropriate advice for the subject. The server 151 transmits the result of the estimation and the advice to the mobile terminal 150 owned by the subject. Thereby, a system in which the mobile terminal 150 displays, in its display, the result of the estimation and a received advice may be established. The server 151, by using a communication function of the electronic device 100, may collect information from a plurality of users, thereby improving its estimation accuracy. Also, using the mobile terminal 150 as a notification means allows omission of the notification interface 147 of the electronic device 100, thereby enabling further downsizing of the electronic device 100. Also, the server 151 estimates the subject's blood fluidity and the states of the subject's glucose metabolism and lipid metabolism, thus reducing the calculation burden of the controller 143 of the electronic device 100. Also, the server 151 may store the information obtained from the subject in the past, reducing the burden on the memory 145 of the electronic device 100. Accordingly, the electronic device 100 may be further downsized and simplified. Further, calculation speed is improved.

Although in the system according to the present embodiment described above the electronic device 100 and the mobile terminal 150 are connected to each other through the communication network via the server 151, the system according to the present embodiment is not limited thereto. The electronic device 100 and the mobile terminal 150 may be connected to each other through the communication network, without using the server 151.

Second Embodiment

Figure 12:
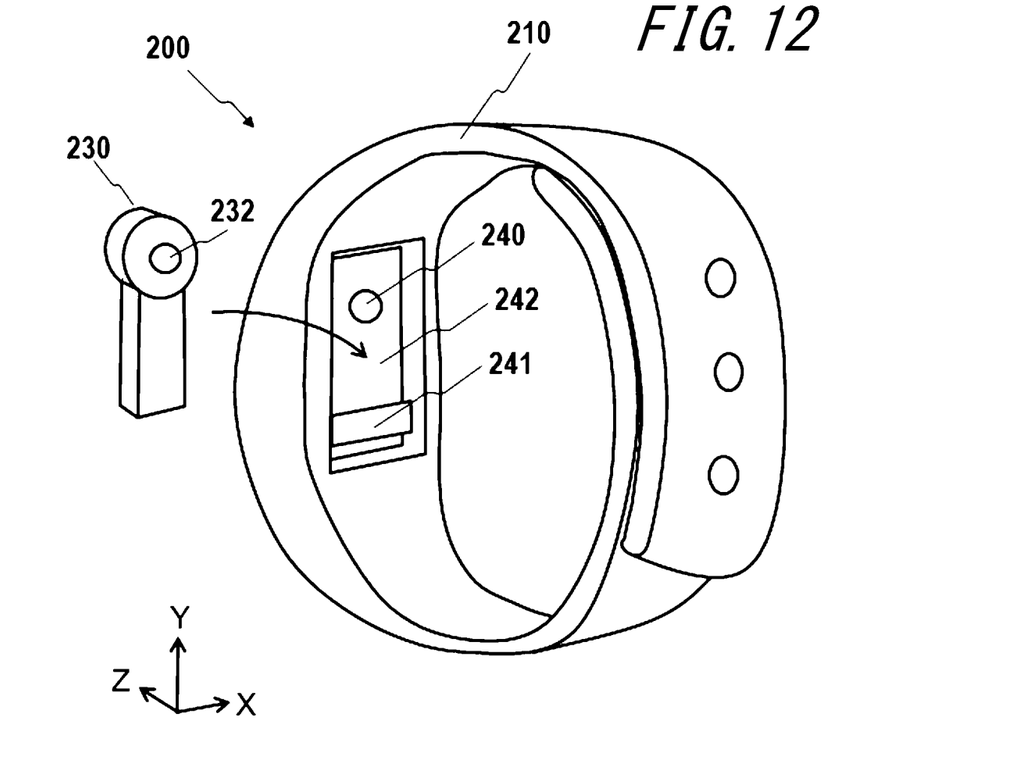
FIG. 12 is a schematic diagram illustrating a configuration of an electronic device according to a second embodiment.

FIG. 12 is a schematic diagram illustrating a configuration of an electronic device according to a second embodiment. Hereinafter, descriptions of elements the same as those of the first embodiment will be omitted, and different elements will be described.

An electronic device 200 according to the second embodiment includes a wearing portion 210 and a sensor unit 230. The electronic device 200 measures the biological information of the subject when worn by the subject. The biological information measured by the electronic device 200 is the pulse wave of the subject that is measurable by the sensor unit 230. According to the present embodiment, the electronic device 200 is worn on, for example, the wrist of the subject to acquire the pulse wave.

According to the present embodiment, the wearing portion 210 is a strip-like band made of, for example, a flexible resin. The wearing portion 210 includes a recess 242. The electronic device 200 is worn by the subject with the sensor unit 230 inserted into the recess 242. The recess 242 has a size and a depth to accommodate the sensor unit 230. An elastic body 240 and an attaching portion 241 are arranged in the recess 242. The sensor unit 230 inserted in the recess 242 is supported by the attaching portion 241 arranged in the recess 242. The sensor unit 230 contacts the elastic body 240 in a state where it is supported by the attaching portion 241. The elastic body is made of resin having an appropriate elastic modulus.

Figure 13:
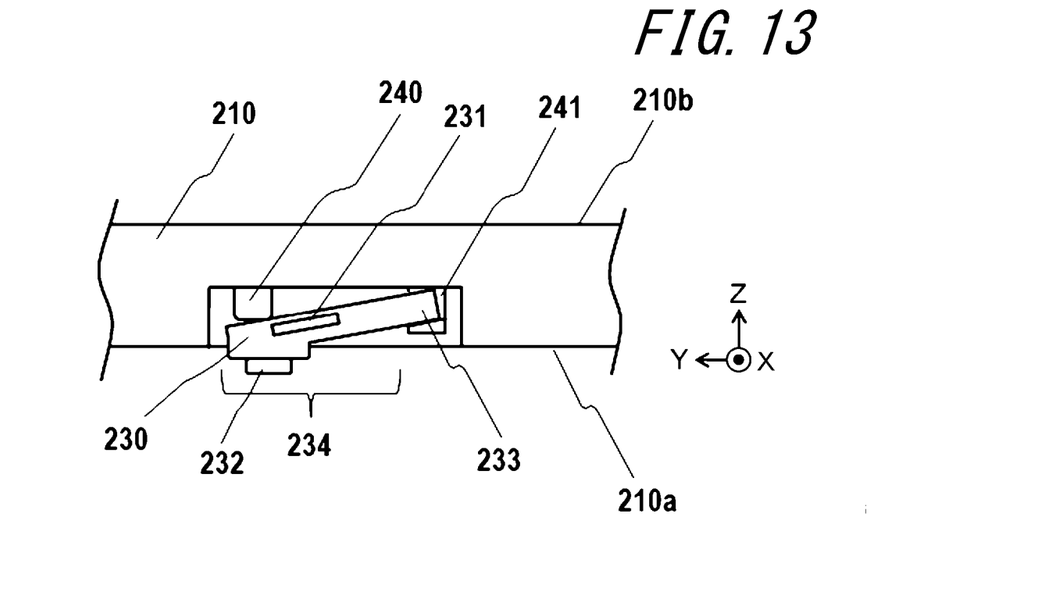
FIG. 13 is a cross-sectional diagram illustrating a configuration of the electronic device according to the second embodiment in the vicinity of a sensor unit.

FIG. 13 is a cross-sectional diagram illustrating a configuration of the electronic device 200 illustrated in FIG. 12 in the vicinity of the sensor unit 230. FIG. 13 also illustrates the wearing portion 210 in the vicinity of the sensor unit 230.

The sensor unit 230 includes an angular velocity sensor 231 configured to detect displacement of the sensor unit 230. The angular velocity sensor 231 needs to simply detect angular displacement of the sensor unit 230. The sensor provided to the sensor unit 230 is not limited to the angular velocity sensor 231 and may include, for example, an acceleration sensor, an angle sensor, or other motion sensors. The sensor unit 230 may include a combination of these sensors.

For measurement of the pulse wave, the subject wraps the waring portion 210 around the wrist in such a manner that a pulse contacting portion 232 contacts the measured part. The electronic device 200, while on the wrist of the subject, measures the pulse wave of blood flowing through the ulnar artery or the radial artery.

The wearing portion 210 includes a rear face 210a to contact the subject's wrist when the subject is wearing the electronic device 100, and a front face 210b on an opposite side to the rear face 210a. The wearing portion 210 includes the recess 242 formed in the rear face 210a. In a state where the elastic body 240 is not compressed, the sensor unit 230 has one end protruding to the rear face 210a from the recess 242 and is supported by the attaching portion 241. The one end of the sensor unit 230 is provided with a pulse contact portion 232. The pulse contact portion 232 is a protrusion having a diameter slightly larger than a diameter of the artery of the subject, e.g., 3 to 10 mm. The subject brings the pulse contact portion 232 into contact with the measured part. The pulse contact portion 232 facilitates contact of the sensor unit 230 with the measured part.

The sensor unit 230 includes a supported portion 233 supported by the attaching portion 241. The sensor unit 230 includes a displacement portion 234 to be displaced in accordance with the pulse wave of the subject. The displacement portion 234 of the sensor unit 230 may be displaceable in accordance with the pulse wave of the subject in a direction substantially perpendicular to a plane of the rear face 210a (Z direction in the figure). The supported portion 233 of the sensor unit 230 is supported by the attaching portion 241 in the wearing portion 210 in such a manner that the displacement portion 234 of the sensor unit 230 is displaced in accordance with the pulse wave. According to the present embodiment, the attaching portion 241 is in the form of, for example, a resin pocket into which the supported portion 233 of the sensor unit 230 is insertable. Because the displacement portion 234 of the sensor unit 230 is displaced about the supported portion 233 serving as an axis, the electronic device 200 is able to detect the pulse wave from a change in an angle of the sensor unit 230.

The sensor unit 230 contacts the wearing portion 210 via the elastic body 240 and is displaceable in accordance with the pulse wave of the subject. The elastic body 240 may be selected from a resin or a spring that has a suitable elastic modulus to extend and contract in accordance with the pulse wave while maintaining the sensor unit 230 in contact with the measured part. The elastic body 240 may utilize, for example, a silicone resin, an epoxy resin, a nylon resin, or the like. The electronic device 200 is worn by the subject in such a manner that, for example, the pulse contact portion 232 contacts the measured part. The subject may adjust a position of the wearing portion 210 such that the pulse contact portion 232 contacts the skin above the ulnar artery or the radial artery. The wearing portion 210 of the electronic device 200 is adjustable to fit on the wrist of the subject.

Figure 14:
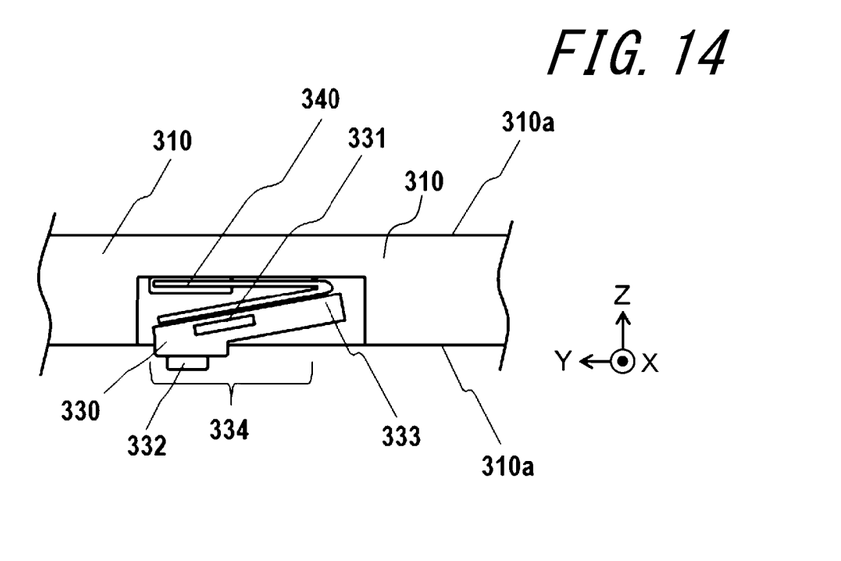
FIG. 14 is a cross-sectional diagram illustrating a configuration of the electronic device according to the second embodiment in the vicinity of the sensor unit when another elastic body is used.

FIG. 14 is a cross-sectional diagram illustrating a configuration of the electronic device according to the second embodiment in the vicinity of the sensor unit in a case where a flat spring is used as the elastic body. That is, the elastic body according to the present embodiment is configured as a flat spring 340. A wearing portion 310 includes a rear face 310a to contact the subject's wrist when the electronic device is worn by the subject, and a front surface 310b on an opposite side from the rear surface 310a. The wearing portion 310 includes the flat spring 340 disposed in a recess formed in the rear surface 310a. One of the surfaces of the flat spring 340 is supported by the wearing portion 310, and the other surface has the sensor unit 330 attached thereto. The flat spring 340 bends in accordance with the pulse wave of the subject. A supported portion 333 of the sensor unit 330 is positioned near a folded portion of the flat spring 340. A displacement portion 334 of the sensor unit 330 is a portion to be displaced in accordance with the pulse wave of the subject. The displacement portion 334 of the sensor unit 330, similarly to the embodiment illustrated in FIG. 13, is displaceable in the direction substantially perpendicular to a plane of the rear face 310a (Z direction in the figure) in accordance with the pulse wave of the subject. The sensor unit 330 includes an angular velocity sensor 331 configured to detect the displacement of the sensor unit 330. For measurement of the pulse wave, the subject wraps the wearing portion 31 around the wrist in such a manner that a pulse contact portion 332 of the sensor unit 330 comes into contact with the measured part. According to the present embodiment also, the displacement portion 334 of the sensor unit 330 is displaced about the supported portion 333 acting as an axis, thus enabling the electronic device having the flat spring 340 serving as the elastic body to detect the pulse wave from the change in the angle of the sensor unit 330. The flat spring 340 has an optimum spring constant to deform in accordance with the pulse wave while maintaining the sensor unit 330 in contact with the measured part. The flat spring 340 may be made of, for example, stainless steel, brass, phosphor bronze, beryllium copper, or the like.

By virtue of the sensor capable of accurately acquiring movement of the displacement portion 334 in accordance with the pulse wave, the electronic device according to the present embodiment is able to accurately measure the pulse wave. Also, by virtue of the electronic device according to the present embodiment being wearable by the subject, continuous measurement of the pulse wave is possible and changes in the state of health of the subject can be known on a real-time basis. Also, the electronic apparatus according to the present embodiment is capable of measurement without strongly pressing the blood vessel, thus reducing fatigue of the subject wearing the electronic device for a long period and offering excellent wearability. Further, by virtue of being less likely to be affected by disturbance of the blood flow due to vascular compression at the measured part, the electronic device according to the present embodiment may accurately obtain the pulse wave.

Third Embodiment

Figure 15:
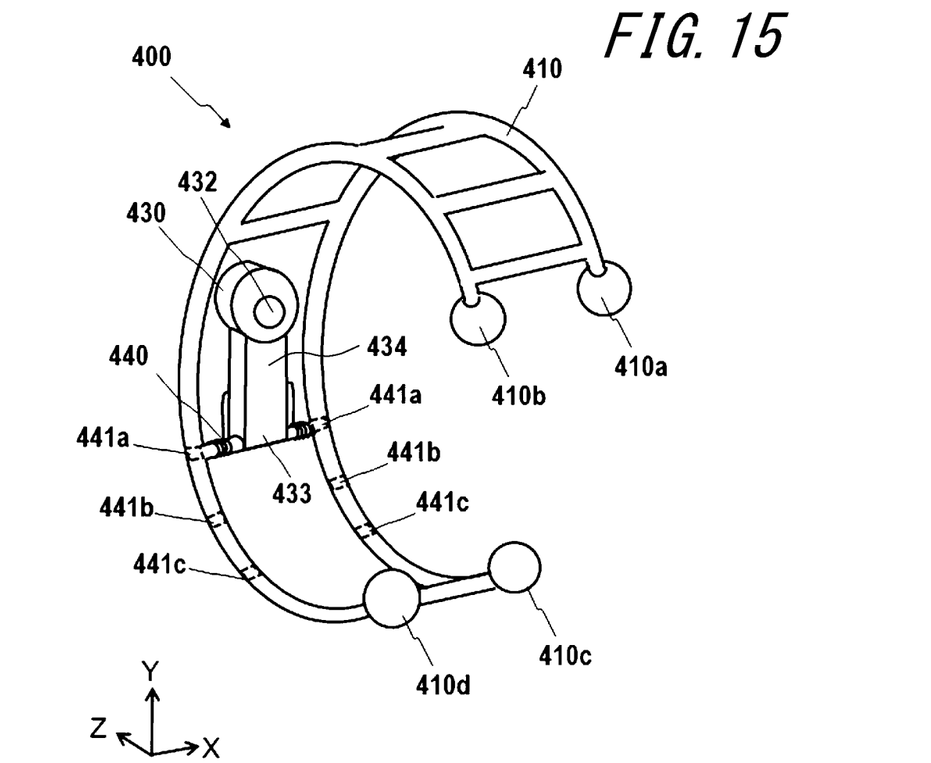
FIG. 15 is a schematic diagram illustrating a configuration of an electronic device according to a third embodiment.

FIG. 15 is a schematic diagram illustrating a configuration of an electronic device according to a third embodiment. Hereinafter, descriptions of elements the same as those of the first or second embodiment will be omitted, and different elements will be described.

An electronic device 400 according to the third embodiment includes a wearing portion 410 and a sensor unit 430. The electronic device 400 measures the pulse wave of the subject when worn on the wrist of the subject.

According to the present embodiment, the wearing portion 410 is formed, for example, by a metal having spring-like properties. For example, the wearing portion 410 is shaped as an open-ended bracelet. The subject pushes open the open ends of the wearing portion 410 enclosed by pads 410*a* to 410*d*, and inserts the wrist in the wearing portion 410. The subject wears the wearing portion 410 in such a manner that a pulse contact portion 432 comes into contact with the skin above the radial artery or the ulnar artery. The wearing portion 410 is worn on the subject's wrist with the open ends enclosed by the pads 410*a* to 410*d* pushed open. By virtue of the spring-like properties of the wearing portion 410, the electronic device 400 may be worn on the subject's wrist. The sensor unit 430 is attached to an attaching portion 441*a* formed on the wearing portion 410 via a helical torsion spring 440 serving as the elastic body. Although the helical torsion spring 440 is used as the elastic body according to the present embodiment, the elastic body is not limited thereto but may be a flat spring, rubber, or the like. The wearing portion 410 includes a plurality of attaching portions 441*a* to 441*c*. The sensor unit 430 and the helical torsion spring 440 may be selectively attached to one of the attaching portions 441*a* to 441*c* in a detachable manner. In the electronic device 400 according to the present embodiment, the sensor unit 430 is detachably attached to one of the plurality of attaching portions 441*a* to 441*c*. Therefore, a position of the sensor unit 430 can be adjusted in accordance with the size of the subject's wrist as well as the position of the artery. Also, the subject can adjust the wearing position of the wearing portion 410 on the wrist such that the pulse contact portion 432 comes into contact with the measured part, while viewing the wearing portion 410. In a state where the helical torsion spring 440 is not extending or contracting, an end of the sensor unit 430 protrudes to the wrist when worn (in a −Z direction in FIG. 15) and is supported by the attaching portion 441*a*. The protruding end of the sensor unit 430 includes the pulse contact portion 432. A displacement portion 434 of the sensor unit 430 is displaceable in the Z direction in the figure in accordance with the pulse wave of the subject. A supported portion 433 of the sensor unit 430 is supported by the attaching portion 441*a* via the helical torsion spring 440 in such a manner as to allow displacement of the displacement portion 434 of the sensor unit 430 in accordance with the pulse wave. The sensor unit 430 is in contact with the wearing portion 410 via the helical torsion spring 440 and is displaceable in accordance with the pulse wave of the subject. The helical torsion spring 440 has an appropriate spring constant to deform in accordance with the pulse wave while maintaining its contact with the measured part. The electronic device 400 is worn by the subject in such a manner that, for example, the pulse contact unit 432 comes into contact with the measured part. The electronic device 400 may be prepared with a plurality of wearing portions 410 with different sizes to fit on the wrist of the subject.

By virtue of the sensor capable of accurately acquiring the movement of the displacement portion 434 in accordance with the pulse wave, the electronic device according to the present embodiment is able to accurately measure the pulse wave. Also, by virtue of the electronic device according to the present embodiment being wearable by the subject, continuous measurement of the pulse wave is possible and changes in the state of health of the subject can be known on a real-time basis. Also, the electronic apparatus according to the present embodiment is capable of measurement without strongly pressing the blood vessel, thus reducing fatigue of the subject wearing the electronic device for a long period and offering excellent wearability. Further, by virtue of being less likely to be affected by disturbance of the blood flow due to vascular compression at the measured part, the electronic device according to the present embodiment may accurately obtain the pulse wave.

Specific embodiments are described above for the purpose of complete and clear disclosure. However, the appended claims should not be construed as limited to the above embodiments but implement all variations and alternative configurations that may be created by those who are skilled in the art within the scope of the fundamentals presented herein.

For example, although in the first embodiment described above the sensor unit 130 includes the angular velocity sensor 131, the electronic device 100 of the disclosure is not limited thereto. The sensor unit 130 may include an optical pulse wave sensor having an optical emitter and an optical detector, or may include a pressure sensor. Also, the electronic device 100 may be worn elsewhere other than on the wrist. The electronic device 100 simply needs the sensor unit 130 to be positioned above the artery such as on the neck, ankle, thigh, ear, and the like. The same applies to the second and third embodiments.

For example, although in the first embodiment described above the state of the subject's glucose metabolism and lipid metabolism are estimated on the basis of the first and second extreme values of the pulse wave index, the electronic device of the disclosure is not limited thereto. There may be cases where one of, or none of the extreme values appear. In this case, the state of the subject's glucose metabolism and lipid metabolism are estimated on the basis of an overall tendency (e.g., an integrated value, Fourier transform, and the like) of the change in the pulse wave index over time. Alternatively, the state of the subject's glucose metabolism and lipid metabolism may be estimated based on a time range in which the pulse wave index becomes equal to or smaller than a predetermined value, instead of by extracting the extreme values of the pulse wave index. The same applies to the second and third embodiments.

For example, although in the first embodiment described above the blood fluidity before and after a meal is estimated, the electronic device of the disclosure is not limited thereto. The electronic device of the disclosure may estimate the blood fluidity before, after, and during exercise, or before, after, and during bath time.

In the first to third embodiments described above, a natural frequency of the sensor unit may be set to be close to a frequency of the pulse wave to be acquired. For example, when the frequency of the pulse wave to be acquired is 0.5 to 2 Hz (pulse rate 30 to 120), the sensor unit may be set to have the natural frequency of somewhere within a range of 0.5 to 2 Hz. The natural frequency of the sensor unit may be optimized by adjusting a length or weight of the sensor unit, the elastic modulus, or the spring constant of the elastic body. Such optimization of the natural frequency of the sensor unit enhances the accuracy of the measurement by the electronic device of the disclosure.

The invention claimed is:

1. An electronic device comprising:
a wearing portion to be worn by a subject; and
a sensor unit including a sensor configured to detect a pulse wave of the subject, wherein
the sensor unit includes a first side extending in a longitudinal direction of the sensor unit and a second side extending in a direction transverse to the longitudinal direction of the sensor unit when viewed along a normal direction with respect to a surface of the sensor unit that faces a measured part of the subject when the wearing portion is worn by the subject, wherein
a length of the first side extending in the longitudinal direction of the sensor unit is longer than a length of the second side extending in the transverse direction,
a first end of the sensor unit, in the longitudinal direction of the sensor unit, is a displacement portion configured to contact a measured part of the subject and to be displaced in accordance with the pulse wave of the subject when the wearing portion is worn by the subject, and a second end of the sensor unit, in the longitudinal direction of the sensor unit, is a supported portion attached to an attaching portion of the wearing portion, wherein
the sensor is provided directly on the displacement portion of the sensor unit, and the displacement portion is displaced about the supported portion serving as an axis.

2. The electronic device according to claim 1, wherein the sensor unit contacts the wearing portion via an elastic body.

3. The electronic device according to claim 1, wherein the supported portion of the sensor unit is supported by the attaching portion of the wearing portion to avow displacement of the displacement portion in accordance with the pulse wave of the subject.

4. The electronic device according to claim 1, wherein the sensor detects an angular change of the sensor unit in accordance with the pulse wave of the subject.

5. The electronic device according to claim 1, wherein a natural frequency of the sensor unit is substantially equal to an expected frequency of the pulse wave of the subject.

6. The electronic device according to claim 1, wherein a natural frequency of the sensor unit is within a range of 0.5 Hz to 2 Hz.

7. The electronic device according to claim 1, wherein the sensor unit is detachably attached to the attaching portion of the wearing portion.

8. The electronic device according to claim 7, wherein the attaching portion is selected from a plurality of attaching portions of the wearing portion.

9. The electronic device according to claim 1, wherein the sensor unit is configured to contact skin over the radial artery or the ulnar artery when the wearing portion is worn on the wrist of the subject.

10. The electronic device according to claim 1, further comprising a controller configured to calculate an index on the basis of the pulse wave detected by the sensor,
wherein the controller estimates a glucose metabolism state or a lipid metabolism state of the subject based on the index calculation.

11. The electronic device according to claim 10, wherein the index is an index associated with a reflected wave.

12. The electronic device according to claim 1, further comprising a controller configured to calculate an index on the basis of the pulse wave detected by the sensor,
wherein the controller estimates blood fluidity of the subject based on the index calculation.

13. The electronic device according to claim 12, wherein the index is an index associated with a reflected wave.

* * * * *